(12) United States Patent
Zhang et al.

(10) Patent No.: US 9,162,897 B2
(45) Date of Patent: Oct. 20, 2015

(54) METHOD OF PREPARING SILVER LOADED ACTIVATED CARBON FIBER

(71) Applicants: Feng Zhang, Zhangjiagang (CN); Lirong Yao, Zhangjiagang (CN)

(72) Inventors: Feng Zhang, Zhangjiagang (CN); Lirong Yao, Zhangjiagang (CN)

(73) Assignee: Zhangjiagang Nellnano Technology Co., Ltd, Zhangjiagang (CN)

( * ) Notice: Subject to any disclaimer, the term of this patent is extended or adjusted under 35 U.S.C. 154(b) by 49 days.

(21) Appl. No.: 14/243,953

(22) Filed: Apr. 3, 2014

(65) Prior Publication Data

US 2014/0335200 A1 Nov. 13, 2014

(30) Foreign Application Priority Data

May 9, 2013 (CN) .......................... 2013 1 0167513

(51) Int. Cl.

| | |
|---|---|
| *C01B 31/08* | (2006.01) |
| *C01B 31/12* | (2006.01) |
| *A01N 59/16* | (2006.01) |
| *A01N 25/34* | (2006.01) |
| *D06M 11/71* | (2006.01) |
| *D06M 15/03* | (2006.01) |
| *D06M 16/00* | (2006.01) |
| *D01F 1/10* | (2006.01) |
| *D01F 9/16* | (2006.01) |
| *D06M 101/06* | (2006.01) |

(52) U.S. Cl.
CPC .............. *C01B 31/125* (2013.01); *A01N 25/34* (2013.01); *A01N 59/16* (2013.01); *D01F 1/103* (2013.01); *D01F 9/16* (2013.01); *D06M 11/71* (2013.01); *D06M 15/03* (2013.01); *D06M 16/00* (2013.01); *C01B 31/08* (2013.01); *D06M 2101/06* (2013.01)

(58) Field of Classification Search
CPC ............................... C01B 31/08; C01B 31/125
USPC .............................. 423/447.1, 447.2; 502/417
See application file for complete search history.

(56) References Cited

FOREIGN PATENT DOCUMENTS

| | | |
|---|---|---|
| CN | 1480584 A | 3/2004 |
| CN | 1726781 A | 2/2006 |
| CN | 101387001 A | 3/2009 |
| CN | 102133420 A | 7/2011 |

OTHER PUBLICATIONS

Wan et al., Adsorption of *Escherichia coli* to activated carbon fibers supporting silver, Acta Scien Tiae Circumstan Tiae, vol. 19, No. 3, May 1999, pp. 328-331.

*Primary Examiner* — Richard M Rump

(57) ABSTRACT

A method of preparing a silver loaded activated carbon fiber includes the following steps. A viscose fiber is treated with a hydroxyalkyl cyclodextrin aqueous solution to obtain a hydroxyalkyl cyclodextrin loaded viscose fiber. The hydroxyalkyl cyclodextrin loaded viscose fiber is then treated with a silver salt aqueous solution to obtain a hydroxyalkyl cyclodextrin and silver salt loaded viscose fiber. The hydroxyalkylated cyclodextrin and silver salt loaded viscose fiber is heated in deionized water at 80 to 100° C. to obtain a silver loaded viscose fiber. The silver loaded viscose fiber is treated with a disodium hydrogen phosphate aqueous solution and then heated under nitrogen at 400 to 600° C. to obtain a silver loaded carbon fiber. The silver loaded carbon fiber is heated under nitrogen and water vapor at 900 to 1,200° C. to obtain the silver loaded activated carbon fiber.

9 Claims, 1 Drawing Sheet

METHOD OF PREPARING SILVER LOADED ACTIVATED CARBON FIBER

The present invention claims priority to Chinese Patent Application No. 201310167513.7, filed on May 9, 2013.

BACKGROUND OF THE INVENTION

1. Field of the Invention

The present invention relates to a method of preparing silver loaded activated carbon fiber and the silver loaded activated carbon fiber prepared thereof.

2. Discussion of the Related Art

Activated carbon fiber (ACF), also known as the fibrous activated carbon, is an adsorbent material having a large specific surface area and a narrow pore size distribution. Activated carbon fiber has a fast adsorption-desorption rate and a large adsorption capacity, can be easily processed into different shapes, such as carpets, cloth, and paper, and is acid, base, and corrosion resistant. Activated carbon fiber has been used in widely in environmental protection, catalyst, medicine, and various other fields.

Activated carbon fiber can also used for air and water filtration. Activated carbon fiber, however, does not have antimicrobial properties. Silver loaded activated carbon fiber overcomes the shortcomings of activated carbon fiber, and possesses both adsorption and antimicrobial properties. Silver loaded activated carbon fiber can be used in air and water filtration, antimicrobial dressings, and other various fields.

In related art, there are two type of methods of preparing silver loaded activated carbon fiber. In the first type of methods, silver is first loaded onto the fibers, and the fiber is then carbonized and activated. Chinese patent application publication CN 102133420 describes a such method. This type of methods have the following shortcomings. The silver is not adequately loaded onto the fibers, and after the fiber is carbonized and activated, the silver is not evenly distributed on the surface of the activated carbon fiber, and does not have uniform particle size. This results in poor antimicrobial properties.

In the second type of methods, the fiber is first carbonized and activated, and silver is the loaded onto the activated carbon fiber. Chinese patent application publications CN 1726782, CN 101387001, and CN 1480584 and Acta Scien Tiae Circumstan Tiae, Vol. 19, No. 3, pages 328-331 describe such methods. These methods have the following shortcomings. The binding between the silver particles and the activated carbon fiber is weak, and the loaded silver particles are often disassociated from the activated carbon fiber during use. This results in short use life of the silver loaded activated carbon fiber and poor antimicrobial properties.

Accordingly, there exists a need for developing a silver loaded activated carbon fiber with evenly distributed, uniform, and stable silver particles and its preparation method.

SUMMARY OF THE INVENTION

An advantage of the present invention is a method of preparing a silver loaded activated carbon fiber including the following steps: (1) treating a viscose fiber with a hydroxyalkyl cyclodextrin aqueous solution to obtain a hydroxyalkyl cyclodextrin loaded viscose fiber, (2) treating the hydroxyalkyl cyclodextrin loaded viscose fiber with a silver salt aqueous solution to obtain a hydroxyalkyl cyclodextrin and silver salt loaded viscose fiber, (3) heating the hydroxyalkylated cyclodextrin and silver salt loaded viscose fiber in deionized water at 80 to 100° C. to obtain a silver loaded viscose fiber, (4) treating the silver loaded viscose fiber with a disodium hydrogen phosphate aqueous solution and then heating the treated silver loaded viscose fiber under nitrogen at 400 to 600° C. to obtain a silver loaded carbon fiber, and (5) heating the silver loaded carbon fiber under nitrogen and water vapor at 900 to 1,200° C. to obtain the silver loaded activated carbon fiber.

In one embodiment of the present application, hydroxyalkyl cyclodextrin is hydroxyethyl cyclodextrin or hydroxypropyl cyclodextrin; and the silver salt is silver nitrate or silver acetate.

In one embodiment of the present application, in the step (1), the concentration of the hydroxyalkyl cyclodextrin aqueous solution is 0.01 to 0.1 gram/liter, and treating the viscose fiber is for 5 to 10 minutes.

In one embodiment of the present application, in the step (2), the concentration of the silver salt aqueous solution is 0.01 to 0.1 gram/liter, and heating the hydroxyalkyl cyclodextrin loaded viscose fiber is for 5 to 10 minutes.

In one embodiment of the present application, in the step (3), heating the hydroxyalkylated cyclodextrin and silver salt loaded viscose fiber is for 1 to 10 minutes, and the silver salt is reduced to silver.

In one embodiment of the present application, in the step (4), the concentration of the disodium hydrogen phosphate aqueous solution is 10 to 40 gram/liter, treating the silver loaded viscose fiber with the disodium hydrogen phosphate aqueous solution is for 4 to 16 hours, and heating the silver loaded viscose fiber is for 10 to 30 minutes.

In one embodiment of the present application, in the step (5), heating the silver loaded carbon fiber is for 10 to 30 minutes.

In one embodiment of the present application, in the step (5), the pressure of the water vapor is 0.2 to 0.4 MPa.

Yet another advantage of the present invention is the silver loaded activated carbon fiber prepared according to the method of claim 1.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
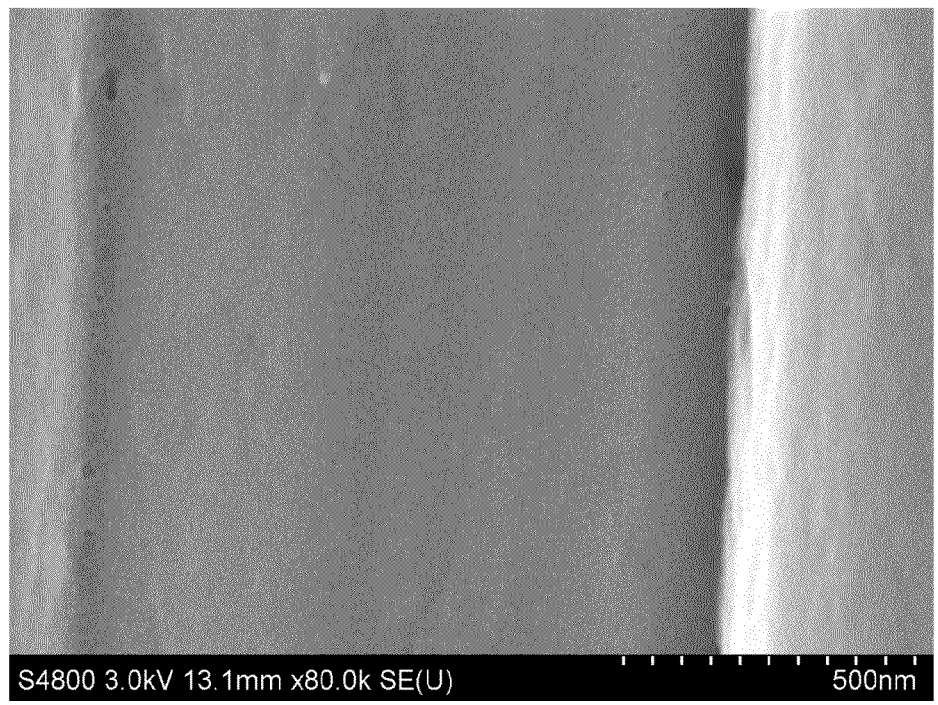
FIG. 1 is the scanning electron micrograph (SEM) of the activated carbon fiber.

Reference will now be made in detail to embodiments of the present invention, example of which is illustrated in the accompanying drawings.

The present invention provides a method of preparing a silver loaded activated carbon fiber. The silver loaded activated carbon fiber has evenly distributed, uniform, and stable silver particles and good antimicrobial activities. The method includes the following steps.

Viscose fiber was cleaned with deionized water, and was then treated an aqueous solution of hydroxyalkyl cyclodextrin. The hydroxyalkyl cyclodextrin can be hydroxyethyl cyclodextrin or hydroxypropyl cyclodextrin. The concentration of the hydroxyalkyl cyclodextrin solution can be 0.005 to 0.5 gram/liter, preferably 0.01 to 0.10 gram/liter. The concentration can be, for example, 0.005, 0.01, 0.02, 0.03, 0.04, 0.05, 0.06, 0.07, 0.08, 0.09, 0.10, 0.20, 0.30, 0.40, or 0.50 gram/liter. The treatment can be 1 to 30 minutes, preferably 5 to 10 minutes. The treatment can be, for example, 1, 5, 10, 15, 20, 25, or 30 minutes. After the treatment, the hydroxyalkyl cyclodextrin aqueous solution was removed to obtain a hydroxyalkyl cyclodextrin loaded viscose fiber.

The hydroxyalkyl cyclodextrin loaded viscose fiber was then treated with an aqueous solution of a silver salt. The silver salt can be silver nitrate, silver acetate, or any other similar silver salts. The concentration of the silver salt is 0.05 to 0.5 gram/liter, preferably 0.01 to 0.1 gram/liter. The concentration can be, for example, 0.005, 0.01, 0.02, 0.03; 0.04, 0.05, 0.06, 0.07, 0.08, 0.09, 0.10, 0.20, 0.30, 0.40, or 0.50 gram/liter. The treatment can be 1 to 30 minutes, preferably 5 to 10 minutes. The treatment can be, for example, 1, 5, 10, 15, 20, 25, or 30 minutes. After the treatment, the silver salt aqueous solution was removed to obtain a hydroxyalkyl cyclodextrin and silver salt loaded viscose fiber.

The hydroxyalkyl cyclodextrin and silver salt loaded viscose fiber was placed in deionized water, and heated at 60 to 100° C., preferably 80 to 100° C. The heating can be, for example, at 60, 65, 70, 75, 80, 85, 90, 95, or 100° C. The heating can be 1 to 30 minutes, preferably, 1 to 10 minutes. The heating can be, for example, 1, 5, 10, 15, 20, 25, or 30 minutes. It is believed that that the silver salt was reduced to silver during the heating. After the heating, water was removed, and resulted fiber was dried to obtain a silver loaded viscose fiber, which is of a golden color.

The silver loaded viscose fiber was treated with an aqueous solution of disodium hydrogen phosphate. The concentration of the disodium hydrogen phosphate solution is 5 to 60 gram/liter, preferably 10 to 40 gram/liter. The concentration can be, for example, 5, 10, 15, 20, 25, 30, 35, 40, 45, 50, 55, or 66 gram/liter. The treatment can be 1 to 24 hours, preferably, 4 to 16 hours. The treatment can be, for example, 1, 2, 3, 4, 5, 6, 7, 8, 9, 10, 11, 12, 13, 14, 15, 16, 17, 18, 19, 20, 21, 22, 23, or 24 hours. After the treatment, the aqueous solution was removed. The resulted fiber was dried and then heated under a nitrogen atmosphere. The heating can be at 300 to 700° C., preferably, 400 to 600° C. The heating can be, for example, 300, 350, 400, 450, 500, 550, 600, 650, or 700° C. The heating can be 5 to 60 minutes, preferably, 10 to 30 minutes. The heating can be, for example, 5, 10, 15, 20, 25, 30, 35, 40, 45, 50, 55, or 60 minutes. After the heating, a silver loaded carbon fiber was obtained.

The silver loaded carbon fiber was then heated at 800 to 1300° C., preferably, 900 to 1200° C. The heating can be, for example, at 800, 850, 900, 950, 1,000, 1,050, 1,100, 1,150, 1,200, 1,250, or 1,300° C. The heating can be under a nitrogen atmosphere and water vapor. The pressure of the water vapor can be 0.2 to 0.4 Mpa. The heating can be 5 to 60 minutes, preferably 10 to 30 minutes. The heating can be, for example, 5, 10, 15, 20, 25, 30, 35, 40, 45, 50, 55, or 60 minutes. After the heating, a silver loaded activated carbon fiber was obtained.

It is believed that the hydroxyalkyl cyclodextrin is evenly attached to the surface of the viscose fiber after the treatment. The hydroxyalkyl cyclodextrin has strong affinity to silver ion. When the hydroxyalkyl cyclodextrin loaded viscose fiber was treated with a silver salt solution, the silver ion was adsorbed to the hydroxyalkyl cyclodextrin. Thus, the silver ion was evenly distributed on the surface of the viscose fiber. When heating the hydroxyalkyl cyclodextrin and silver salt loaded viscose fiber, the hydroxyalkyl cyclodextrin reduced silver salt to silver. The silver can be in the form of silver nanoparticles. It is also believed that the hydroxyalkyl cyclodextrin stabilized the silver formed in the reduction reaction. The prepared silver loaded viscose fiber was then carbonized and activated via heating to provide silver loaded activated carbon fiber.

Because the silver ion was evenly attached to the surface of the viscose fiber, the silver was also evenly distributed on the surface of the viscose fiber after the reduction reaction. Further, the silver also has a uniform particle size. Measurement indicates that the silver particle size is 50 to 500 nm and the silver content is about 1 to 40 gram/kilogram based on the weight of the activated carbon fiber.

After the carbonization and activation, the silver was stably attached to the activated carbon fiber. The silver load activated carbon fiber was stored in a clear bottle at room temperature for 6 months. Antimicrobial tests show that the 6 months old silver load activated carbon fiber has the same antimicrobial activities as the freshly prepared silver load activated carbon fiber.

The silver load activated carbon fiber can be used in air filtration, water filtration, antimicrobial dressings, and other various fields.

Experiments

Scanning electron micrographs were taken by a Hitachi S-4800 Field Emission Scanning Electron Microscope, with an acceleration voltage of 3.0 kV, working distance 9.8 mm, magnification, 80KX. The silver content was measured via ICP-OES (EPA 3052:1996).

Comparative Example 1

100 gram of clean viscose fiber was heated under nitrogen atmosphere at 600° C. for 30 minutes, and the viscose fiber was carbonized to yield a silver loaded carbon fiber. The silver loaded carbon fiber was heated under nitrogen atmosphere and 0.4 MPa water vapor at 1200° C. for 30 minutes to yield activated carbon fiber. FIG. 1 is the scanning electron micrograph (SEM) of the activated carbon fiber.

Example 1

100 gram of clean viscose fiber was treated in 2000 ml of 0.01 gram/liter hydroxypropyl cyclodextrin aqueous solution for 5 minutes. The treated viscose fiber was treated in 2000 ml of 0.01 gram/liter silver nitrate aqueous solution for 5 minutes. The treated viscose fiber was then placed in 2000 ml deionized water and heated at 80° C. for 1 minute. The treated viscose fiber was dried in an oven at 80° C. for 1 hour to obtain a golden colored silver loaded viscose fiber.

The golden colored silver loaded viscose fiber was treated in 200 ml of 10 gram/liter disodium hydrogen phosphate aqueous solution for 4 hours. The silver loaded viscose fiber was then dried an oven at 50° C. for 1 hour. The dried silver loaded viscose fiber was heated under nitrogen atmosphere at 400° C. for 10 minutes, and the viscose fiber was carbonized to yield a silver loaded carbon fiber. The silver loaded carbon fiber was heated under nitrogen atmosphere and 0.2 MPa water vapor at 900° C. for 10 minutes to yield silver loaded activated carbon fiber.

Test shows that the silver content of the silver loaded activated carbon fiber is 2.2 g/kilogram based on the weight of the activated carbon fiber.

Figure 2:
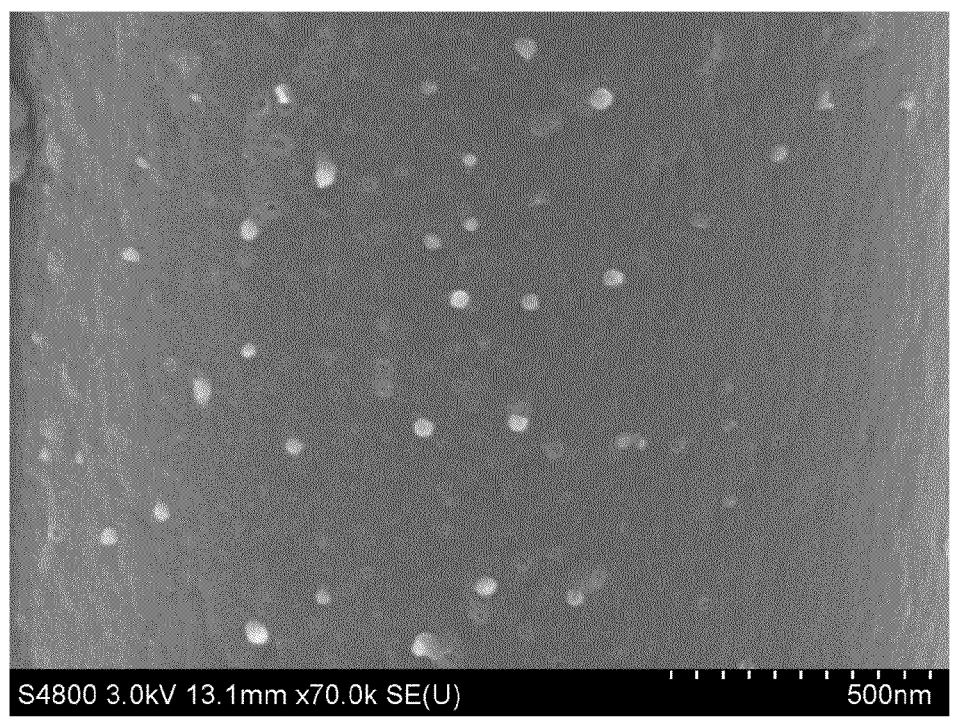
FIG. 2 is the scanning electron micrograph (SEM) of the silver loaded activated carbon fiber.

FIG. 2 is the scanning electron micrograph (SEM) of the silver loaded activated carbon fiber. FIG. 2 shows that the silver particles are evenly distributed on the surface of the activated carbon fiber.

Example 2

100 gram of clean viscose fiber was treated in 2000 ml of 0.1 gram/liter hydroxyethyl cyclodextrin aqueous solution for 10 minutes. The treated viscose fiber was treated in 2000 ml of 0.1 gram/liter silver acetate aqueous solution for 10 minutes. The treated viscose fiber was then placed in 2000 ml deionized water and heated at 100° C. for 10 minutes. The treated viscose fiber was dried in an oven at 80° C. for 1 hour to obtain a golden colored silver loaded viscose fiber.

The golden colored silver loaded viscose fiber was treated in 2000 ml of 40 gram/liter disodium hydrogen phosphate aqueous solution for 16 hours. The silver loaded viscose fiber was then dried an oven at 80° C. for 1 hour. The dried silver loaded viscose fiber was heated under nitrogen atmosphere at 600° C. for 30 minutes, and the viscose fiber was carbonized to yield a silver loaded carbon fiber. The silver loaded carbon fiber was heated under nitrogen atmosphere and 0.4 MPa water vapor at 1200° C. for 30 minutes to yield silver loaded activated carbon fiber.

Test shows that the silver content of the silver loaded activated carbon fiber is 20 gram/kilogram based on the weight of the activated carbon fiber.

Antibacterial Activities

The silver loaded activated carbon fiber (Example 1) and regular activated carbon fiber (Comparative Example 1) were then tested for antibacterial activities against *Staphylococcus aureus* and *Candida albicans*. The carbon fibers were placed in and mixed with the growth medium containing the bacteria, and the colony counts were measure at 0 and 1 hour after the mixing. The results are summarized in Table 1.

As shown in Table 1, the silver loaded activated carbon fiber has superior antibacterial activities when freshly prepared and after 6 months.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of preparing a silver loaded activated carbon fiber comprising the steps of:
   (1) treating a viscose fiber with a hydroxyalkyl cyclodextrin aqueous solution to obtain a hydroxyalkyl cyclodextrin loaded viscose fiber,
   (2) treating the hydroxyalkyl cyclodextrin loaded viscose fiber with a silver salt aqueous solution to obtain a hydroxyalkyl cyclodextrin and silver salt loaded viscose fiber,
   (3) heating the hydroxyalkylated cyclodextrin and silver salt loaded viscose fiber in deionized water at 80 to 100° C. to obtain a silver loaded viscose fiber,
   (4) treating the silver loaded viscose fiber with a disodium hydrogen phosphate aqueous solution and then heating the treated silver loaded viscose fiber under nitrogen at 400 to 600° C. to obtain a silver loaded carbon fiber, and
   (5) heating the silver loaded carbon fiber under nitrogen and water vapor at 900 to 1,200° C. to obtain the silver loaded activated carbon fiber.

2. The method of claim 1, wherein the hydroxyalkyl cyclodextrin is hydroxyethyl cyclodextrin or hydroxypropyl cyclodextrin.

3. The method of claim 1, wherein the silver salt is silver nitrate or silver acetate.

4. The method of claim 1, wherein in the step (1), the concentration of the hydroxyalkyl cyclodextrin aqueous solution is 0.01 to 0.1 gram/liter, and treating the viscose fiber is for 5 to 10 minutes.

5. The method of claim 1, wherein in the step (2), the concentration of the silver salt aqueous solution is 0.01 to 0.1 gram/liter, and heating the hydroxyalkyl cyclodextrin loaded viscose fiber is for 5 to 10 minutes.

TABLE 1

| Bacteria | Carbon Fiber | Colony Counts 0 hour after mixing (cfu/ml) | Colony Counts 1 hour after mixing (cfu/ml) | Antibacterial Activities % | Difference in antibacterial activities |
|---|---|---|---|---|---|
| *Staphylococcus aureus* | Example 1 | $4.2 \times 10^2$ | 210 | >99 (freshly prepared) >99 (after 6 months) | >101 |
| *Staphylococcus aureus* | Comparative Example 1 | $4.2 \times 10^4$ | $4.3 \times 10^4$ | −2 | |
| *Staphylococcus aureus* | Blank | $4.2 \times 10^4$ | $4.3 \times 10^4$ | / | |
| *Candida albicans* | Example 1 | $6.3 \times 10^4$ | <2 | >99 (freshly prepared) >99 (after 6 months) | >112 |
| *Candida albicans* | Comparative Example 1 | $6.3 \times 10^4$ | $6.8 \times 10^4$ | −13 | |
| *Candida albicans* | Blank | $6.3 \times 10^4$ | $6.8 \times 10^4$ | / | |

6. The method of claim 1, wherein in the step (3), heating, the hydroxyalkylated cyclodextrin and silver salt loaded viscose fiber is for 1 to 10 minutes, and the silver salt is reduced to silver.

7. The method of claim 1, wherein in the step (4), the concentration of the disodium hydrogen phosphate aqueous solution is 10 to 40 gram/liter, treating the silver loaded viscose fiber with the disodium hydrogen phosphate aqueous solution is for 4 to 16 hours, and heating the silver loaded viscose fiber is for 10 to 30 minutes.

8. The method of claim 1, wherein in the step (5), heating the silver loaded carbon fiber is for 10 to 30 minutes.

9. The method of claim 1, wherein in the step (5), the pressure of the water vapor is 0.2 to 0.4 MPa.

\* \* \* \* \*